United States Patent [19]
Klearman et al.

[11] Patent Number: 5,464,393
[45] Date of Patent: * Nov. 7, 1995

[54] APPARATUS FOR, AND METHOD OF, CRUSHING A PILL, SUSPENDING THE PILL INGREDIENTS IN A LIQUID, AND ADMINISTERING THE SUSPENSION

[75] Inventors: Jeffrey D. Klearman; Jeffrey J. Bierman; Eli Schachet, all of St. Louis, Mo.

[73] Assignee: Lake Medical Products, Inc., St. Louis, Mo.

[ * ] Notice: The portion of the term of this patent subsequent to Dec. 27, 2011, has been disclaimed.

[21] Appl. No.: 264,628

[22] Filed: Jun. 23, 1994

Related U.S. Application Data

[63] Continuation-in-part of Ser. No. 168,019, Dec. 15, 1993, Pat. No. 5,376,072.

[51] Int. Cl.⁶ ................................................. A61M 37/00
[52] U.S. Cl. .................... 604/82; 604/56; 604/92; 604/218
[58] Field of Search ............................ 604/56–57, 77–79, 604/82–85, 187, 191, 211, 222, 218, 224, 225

[56] References Cited

U.S. PATENT DOCUMENTS

| | | |
|---|---|---|
| 1,165,686 | 12/1915 | McElroy . |
| 4,057,052 | 11/1977 | Kaufman et al. . |
| 4,568,331 | 2/1986 | Fischer et al. . |
| 4,715,854 | 12/1987 | Vaillancourt . |
| 4,765,549 | 8/1988 | Sherman . |
| 5,118,021 | 6/1992 | Flocchi . |
| 5,376,072 | 12/1994 | Klearman et al. . |

OTHER PUBLICATIONS

American Medical Industries brochure entitled "Making Your Medications & Vitamins EZ To Swallow", including enclosure entitled Remembering Your Medications Schedule is EZ.

American Medical Industries sales flier entitled "Welcome to American Medical Industries' Family of EZ-Health™ Products", 1993.

American Medical Industries facsimile transmission to Lake Medical Products regarding EZ-Swallow Pill Crushers & Pill Splitters, Sep. 1, 1993.

Primary Examiner—C. Fred Rosenbaum
Assistant Examiner—Perry E. Van Over
Attorney, Agent, or Firm—Rogers, Howell & Haferkamp

[57] ABSTRACT

A pill crushing syringe is disclosed which includes a barrel and a plunger, with abraded surfaces on each so that a pill placed in the barrel is crushed as the plunger advances within the barrel. The barrel has an aperture located near the closed end with a catheter connected around and extending from the aperture. The plunger has a sealing gland to provide an airtight seal with the barrel so that liquid may be drawn into the barrel through the aperture by withdrawing the plunger from the barrel to thereby suspend the crushed pill in the liquid, and the suspension may be flushed from the barrel by thereafter advancing the plunger into the barrel. In an alternative embodiment, a bi-level barrel has an aperture in spaced relation to the closed end forming a pocket wherein the crushed pill ingredients accumulate. The pocket at the closed end and the separation between the aperture and the barrel closed end helps prevent the medication from escaping the barrel via the catheter prior to aspiration. In still other embodiments, the syringe has a side entry plunger or two opposing plungers.

36 Claims, 5 Drawing Sheets

— 5,464,393 —

APPARATUS FOR, AND METHOD OF, CRUSHING A PILL, SUSPENDING THE PILL INGREDIENTS IN A LIQUID, AND ADMINISTERING THE SUSPENSION

CROSS-REFERENCE TO RELATED APPLICATION

This application is a continuation-in-part of Ser. No. 08/168 019, filed Dec. 15, 1993, now U.S. Pat. No. 5,376,072.

FIELD OF THE INVENTION

This invention relates to an apparatus for, and method of, crushing a pill, mixing the resulting powder with a liquid and administering the suspension.

BACKGROUND AND SUMMARY OF THE INVENTION

In many instances, it is difficult if not impossible to administer medication in capsule form to patients. This is particularly true for patients who may be comatose or otherwise physically unable to swallow the pills. For those people, in the prior art, the pills were ground with a mortar and pestle. The powder was transferred to a liquid-filled container and mixed with the liquid. The suspension was then either swallowed, or a syringe was filled with the suspension and injected into an intravenous tube or other tube generally used in hospital settings.

The prior art technique carried several drawbacks. The most serious of these were the risks of low and unpredictable compliance and cross-contamination. As the pill was crushed in a mortar and then transferred to another container before being administered, a nurse using extreme care could not help but lose some of the pill as residue on the mortar, pestle, etc. Furthermore, this residue would necessarily vary both in quantity and content from dose to dose to thereby perhaps alter the dosage administered from that intended. In extreme situations, this could interfere with achieving the desired medical result.

The undesired, but inescapable, residue also created an unavoidable risk of cross-contamination as the same mortar and pestle were typically re-used for the same and other patients, as well.

Moreover, the prior art technique was very time consuming as the nurse needed to use care and caution to avoid spillage, which translated into increased nurse or medical technician time and expense.

Other pill crushing devices are also known in the prior art. However, similar to the mortar and pestle technique discussed above, these devices were designed to grind or crush the pill in one compartment, transfer the powder to another liquid-filled container where the powder was dissolved or suspended and then administered. These devices similarly carried the risks of contamination, cross-contamination, spillage and waste, and were again time consuming.

The invention disclosed in the parent hereto, as cross-referenced above, overcomes the foregoing problems by providing a pill crushing syringe which is adapted to crush medication, preferably a pill, and mix the resulting powder with liquid all within the syringe itself, and then administer the suspension with the same syringe. Generally the syringe disclosed in the parent includes a barrel and a plunger. The syringe has two opposing abraded surfaces, one on the plunger and one in the barrel bottom, to crush a pill placed in the barrel by the plunger as it is advanced to the bottom of the barrel. The pill could even be "ground" by rotating the plunger within the barrel to achieve a complete breakdown of the pill into small and regularly sized particles. In an alternate embodiment of the invention disclosed in the parent, the bottom of the barrel may be threaded so that it may also be rotated, thereby permitting both abraded surfaces to be positively driven with respect to each other. The barrel includes an aperture and a catheter located at the bottom of the barrel for drawing liquid into the barrel to mix with the crushed pill particles. The plunger includes a sealing gland providing an airtight relationship between the plunger and the barrel to assist in drawing liquid into the barrel by withdrawing the plunger from the barrel when the catheter tip is submerged in the liquid. The suspension of the liquid and crushed pill particles is administered by advancing the plunger into the barrel thereby forcing the suspension through the catheter and into a tube attached to the patient.

Generally, the method of the invention disclosed in the parent comprises providing a pill crushing syringe including a barrel and a plunger with opposing abraded surfaces so that medication, preferably a pill, placed in the barrel is crushed as the plunger is "bottomed" within the barrel, placing a pill into the barrel, crushing the pill, adding liquid to the barrel thereby suspending the powder in the liquid, and flushing the suspension.

The apparatus and method of the parent invention are significant improvements over the prior art in that pills are crushed, the resulting powder mixed with liquid, and the suspension administered all with the same syringe. Because the pill is crushed in a closed container and the powder need not be transferred for mixing with the liquid, the risk of cross-contamination and spillage is greatly reduced while consistency of compliance is achieved. Moreover, the abraded surfaces used to crush the pills are exposed to the liquid drawn into the barrel which provides a "washing" action on the very surfaces used to grind the pill. This helps to minimize residue.

In addition to reducing the risk of waste and contamination, insuring a high dosage compliance rate, and eliminating the problem of cleaning the pestle and mortar, the invention disclosed in the parent saves nurses time allowing more medicinal dosages to be administered within the same time frame in a reliable manner. Further, the syringe may be made of plastic and used only once, thereby eliminating the risk of cross-contamination.

Building on the invention disclosed in the parent, the inventors have improved their earlier pill crushing syringe by providing a bi-level barrel having an open end, a closed end and a cylindrical wall, and a mating bi-level plunger having a tip end. As in the parent, the syringe has two opposing abraded surfaces, one on the plunger tip end and one on the barrel closed end to thereby crush a pill placed in the barrel as the plunger is advanced and rotated within the barrel. The present invention further includes an aperture through the barrel wall in spaced relation to the closed barrel end such that a pocket is formed by the barrel wall and the closed end between the aperture and the closed end. A substantially straight catheter is connected around and extends from the aperture. By holding the syringe upright, the crushed pill ingredients remain in this pocket prior to aspiration, thereby assuring high dosage integrity by prohibiting medication from escaping through the catheter.

In the parent, the preferred location of the aperture is adjacent the barrel closed end, and a "crooked" catheter is preferred to assure no medication escapes prior to aspiration.

The "crooked" catheter arrangement provides quite favorable results. However, the pocket between the aperture and the barrel closed end of the present invention attains equally favorable dosage integrity while allowing the use of a substantially straight catheter. The straight catheter design is better suited for present injection molding technology and thus is significantly less expensive to manufacture.

An alternative embodiment of the present invention provides an alternative means for crushing the pill into a powder. This embodiment provides a bi-level barrel and a bi-level plunger, wherein the barrel further includes a side opening with a hollow side arm extending from the side opening. A reinforced barrel wall section having an interior abraded surface is positioned opposite the side opening. A side entry plunger having an abraded tip end is movable within the side arm and the side entry plunger is adapted to engage the reinforced wall abraded surface as the side entry plunger advances within the hollow arm and into the barrel. A pill placed between the reinforced wall abraded surface and the side entry plunger abraded tip end is crushed as the side entry plunger is advanced into and rotated within the barrel.

Another alternative embodiment provides a cylinder with two plungers having opposing abraded tip ends adapted to crush a pill placed therebetween by advancing the plungers within the cylinder and rotating the plungers in opposite directions. A catheter is connected around and extends from an aperture through the cylinder wall. A space between the two plungers, which encompasses the crushed pill ingredients, may be positioned to be in fluid connection with the aperture thereby allowing aspiration of the pill ingredients.

BRIEF DESCRIPTION OF THE DRAWINGS

In the accompanying drawings which form a part of the specification and are to be read in conjunction therewith, and in which like reference numerals are used to indicate like parts in the various views.

DETAILED DESCRIPTION OF THE PREFERRED EMBODIMENT

Figure 1:
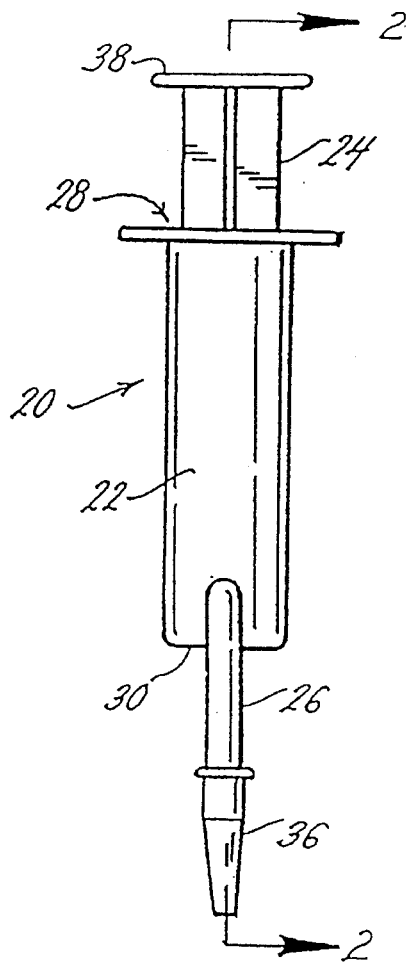
FIG. 1 is an elevation view of the pill crushing syringe constructed according to the principles of the invention disclosed in the parent.
Figure 3:
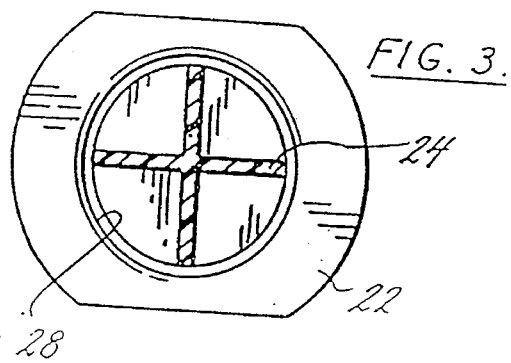
FIG. 3 is a cross-sectional view taken along lines 3—3 in FIG. 2 detailing the construction of the plunger disclosed in the parent.

A pill crushing syringe constructed according to the principles of the invention disclosed in the parent is indicated generally as 20 in FIG. 1. The syringe includes a barrel 22, a plunger 24, and a catheter 26.

Figure 4:
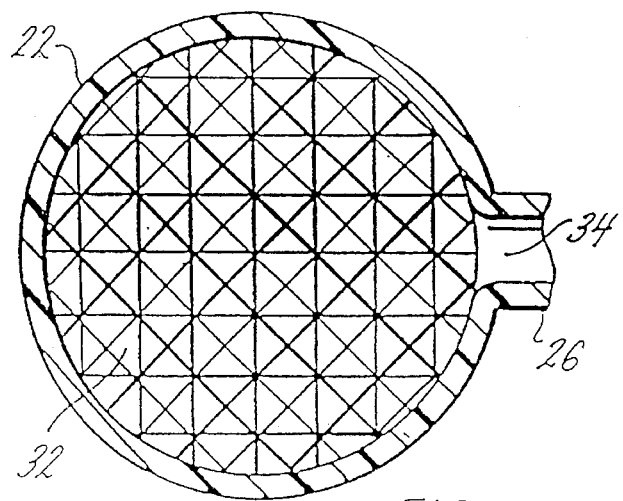
FIG. 4 is a cross-sectional view taken along lines 4—4 in FIG. 2 detailing the construction of the abraded surface.
Figure 2:
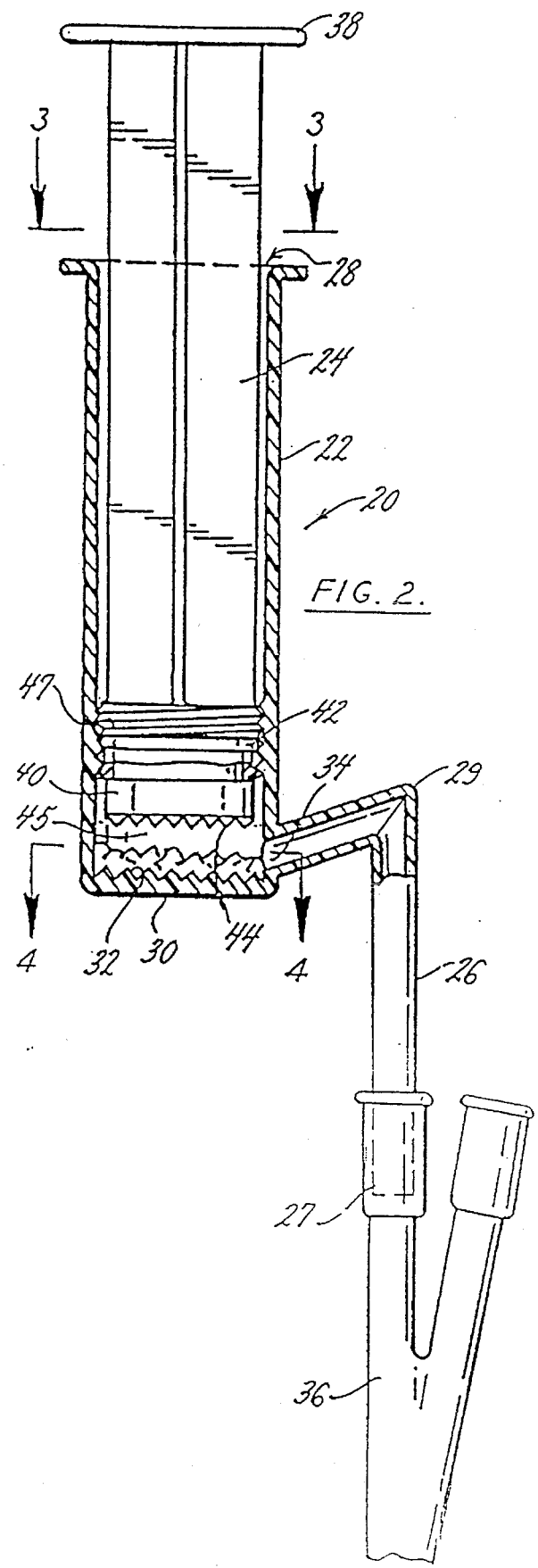
FIG. 2 is a cross-sectional view taken along lines 2—2 in FIG. 1 detailing the interior construction of the syringe disclosed in the parent.

The barrel 22 includes an open end 28 and a preferably flat closed end 30. The closed end 30 has an interior abraded surface 32 which is shown in FIGS. 2 and 4 as preferably serrated. An aperture 34 is formed through the barrel wall preferably adjacent to the abraded surface 32, and the catheter 26 is connected around and extends from aperture 34. The catheter 26 is shown in FIG. 2 as preferably having a crook 29 and including a tip 27 for insertion into a tube 36. In the preferred embodiment, the tube 36 is one commonly used in hospital settings, such as a nasal-gastric tube, gastrostomy tube or a jejunostomy tube, for example.

The plunger 24 includes a handle end 38, a tip end 40, and a sealing gland 42 providing an airtight relationship between the plunger and the barrel. An abraded surface 44 is located on the tip end 40 positioned to engage the barrel abraded surface 32. In the preferred embodiment, the abraded surface 44 is serrated and the sealing gland 42 is preferably integral with the plunger abraded surface 44. A cavity or space 45 is defined within the barrel 22 between the abraded surfaces 32 and 44, and the aperture 34 creates a fluid connection between catheter 26 and cavity 45.

The plunger 24 is removable from the barrel 22 to allow medication, preferably a pill (not shown), to be placed in the barrel. The plunger is also adapted to rotate within the barrel to assist in grinding the pill between abraded surfaces 32 and 44. The barrel 22 and the plunger 24 may include a threaded fitting 47 which advances the plunger into the barrel as the plunger is rotated therein (see FIGS. 2 and 5). The threaded fitting creates a positive grinding action between the abraded surfaces 32 and 44 as the plunger is rotated within the barrel.

The seal created by sealing gland 42 allows liquid to be drawn into the barrel by withdrawing the plunger from the barrel as the catheter tip 27 is submerged in a container of water or the like. The barrel may then be flushed, and the suspension comprising the crushed pill and water evacuated from the syringe, by advancing the plunger into the barrel thereby forcing the suspension through the catheter.

Figure 5:
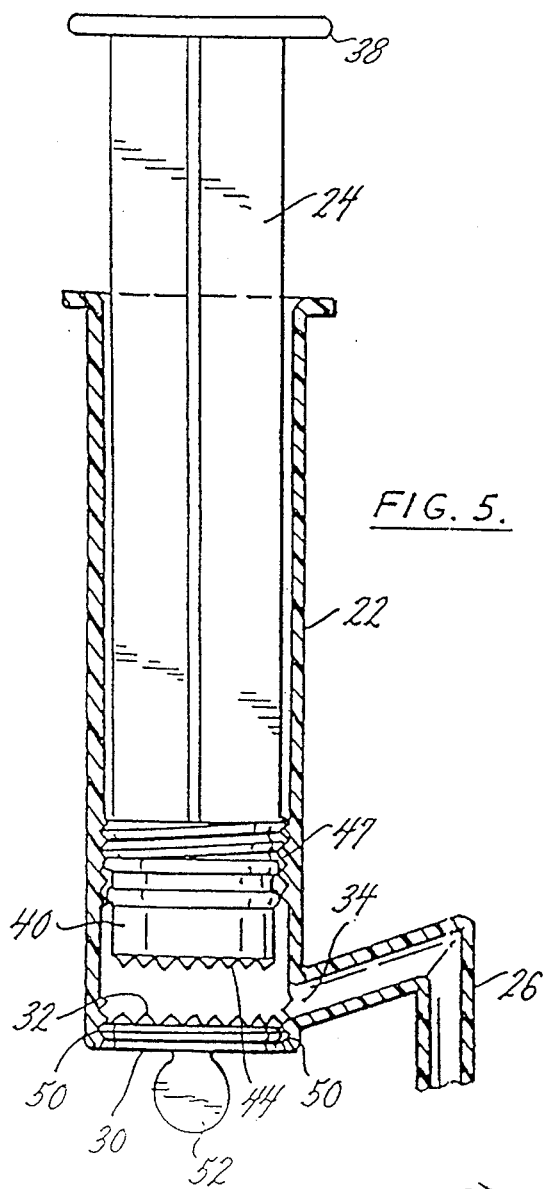
FIG. 5 is a cross-sectional view of the closed bottom constructed according to an alternative embodiment of the invention disclosed in the parent permitting the bottom to be rotated relative to the syringe barrel and plunger.

In an alternative embodiment disclosed in the parent, the closed end 30 is screw thread fastened to the barrel 22 by threaded grooves 50 (see FIG. 5). The closed end 30 is thereby rotatable with respect to the rest of barrel 22 and is removable. The closed end 30 may comprise a thumb screw 52, for example. In this embodiment, the pill may be placed in the barrel 22 by removing the closed end 30 and the closed end may be rotated to facilitate crushing and grinding the pill.

Figure 6:
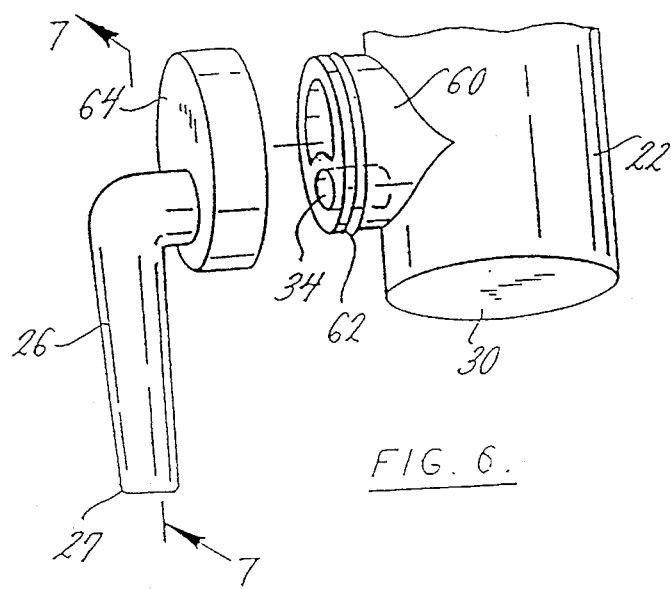
FIG. 6 is an exploded isometric view of a second alternative embodiment of the invention disclosed in the parent illustrating the catheter and cap from the stub housing.

According to a second alternative embodiment disclosed in the parent, the syringe 20 includes means for adjustably sealing the fluid connection between catheter 26 and cavity 45. The adjustable sealing means allows liquid to be temporarily trapped within the cavity. One example of the adjustable sealing means is illustrated in FIG. 6. The barrel 22 further includes a stub housing 60 extending radially, and non-concentrically, from aperture 34, and a retaining lip 62 extends around the outside surface of the stub housing. The aperture 34 extends through the stub housing 60.

Figure 7:
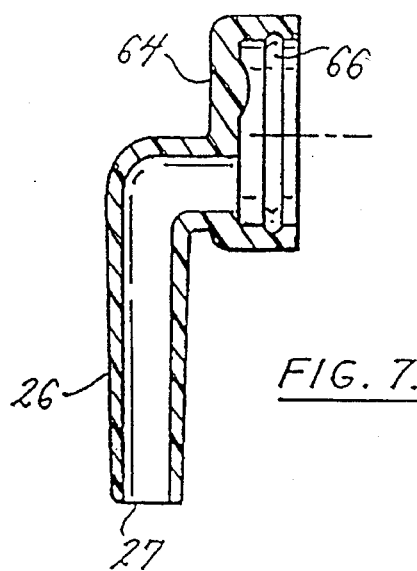
FIG. 7 is a cross-sectional view taken along lines 7—7 in FIG. 6 detailing the catheter position relative to the cap and the groove within the cap.

Catheter 26 includes a cap 64 rotatably coupled to the stub housing and extending radially, and non-concentrically, from the catheter end opposite tip 27. The cap 64 includes a groove 66 (see FIG. 7) appropriately sized to mate with retaining lip 62 thereby creating a liquid-tight seal between the cap and stub housing. The cap 64, being rotatable about the stub housing axis, may be rotated to align the catheter and the aperture for fluid connection, or to mis-align the catheter and aperture to seal the connection.

Figure 8:
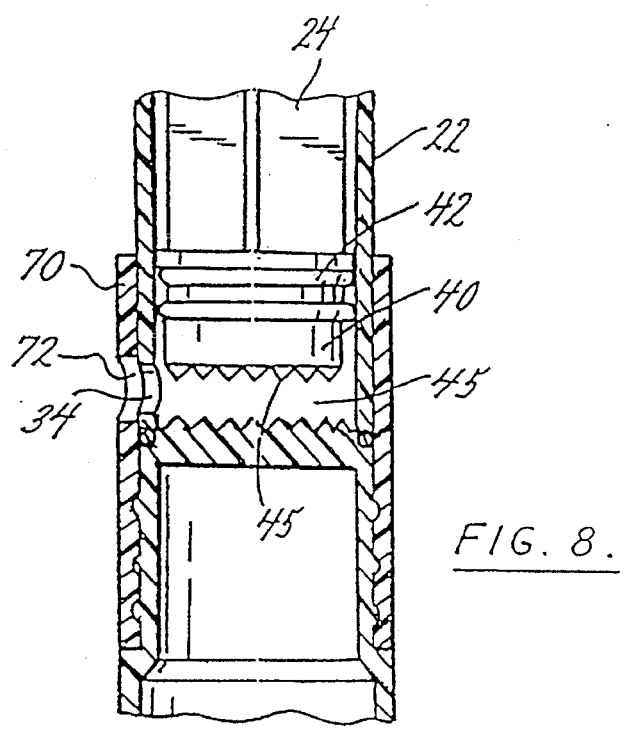
FIG. 8 is a cross-sectional view of a third alternative embodiment of the invention disclosed in the parent illustrating the collar and collar aperture of the adjustable sealing means.

Another example of the adjustable sealing means is illustrated in FIG. 8. A collar 70, having a collar aperture 72, is fitted around the barrel 22 in a substantially fluid tight relationship. The collar 70 is rotatable about the barrel axis and may alternately be rotated to align the collar aperture 72 with the barrel aperture 34, creating a fluid connection therebetween, or to seal the apertures 34 and 72 from each other.

According to the method of the invention disclosed in the parent, the plunger 24 is removed from the barrel 22 and medication, preferably a pill (not shown), is placed in the barrel. The plunger is advanced into the barrel until the pill is lodged snugly between the abraded surfaces 32 and 44. The plunger 24 is then rotated as pressure is exerted thereon and against the pill thereby rotating abraded surface 44 with respect to abraded surface 32 until the pill is crushed and/or ground into a powder 48. The tip 27 of catheter 26 is placed in a liquid, a glass of water for example, and the plunger 24 is withdrawn from the barrel thereby drawing liquid into the barrel cavity 45 to mix with the powder 48 of the crushed pill. The catheter 27 has a crook 29 formed therein to inhibit the free flow of liquid out of the catheter after it is withdrawn from the glass. This helps prevent any of the suspended pill particles from escaping. The syringe 20 may then be shaken to dislodge any powder residue off the abraded surfaces 32 and 44. During shaking, it may be desirable to close off the end of tip 27 to prevent any of the suspension from escaping. The tip 27 of catheter 26 is then inserted into tube 36 and the suspension within the barrel is flushed from the syringe by advancing the plunger into the barrel.

According to an alternative embodiment of the method disclosed in the parent the pill may be placed into the barrel 24 by unscrewing and removing the closed end 30 (see FIG. 5), placing the pill into the barrel, and replacing the closed end. The plunger is then advanced into the barrel until the pill is squeezed snugly between abraded surfaces 32 and 44. The pill may be crushed and/or ground by twisting the closed end 30 within the threaded grooves 50 to thereby rotate abraded surface 32 with respect to abraded surface 44. Further, the barrel 22 can be held steady while simultaneously rotating the plunger within the barrel and twisting the closed end 30 within the threaded grooves 50. This technique provides relative motion between both of the abraded surfaces and the barrel, thereby intensifying the grinding action.

According to a second alternative embodiment of the method disclosed in the parent, once the liquid is drawn into cavity 45 to mix with powder 48, the fluid connection between the catheter 26 and the cavity 45 is temporarily sealed. This allows the syringe to be shaken, violently if necessary, without the possibility of losing liquid or medication from the syringe. Once the powder is fully suspended in the liquid, the catheter-cavity fluid seal is restored and the suspension is flushed from the syringe by advancing the plunger into the barrel.

While the medication placed in the barrel 22 is preferably a pill, the term pill is intended to include tablets, capsules, and other discrete units of medication. The pill may also include particles, powder, or liquid forms of medication. For instance, a capsule may be provided which houses medication within a shell. The medication may be placed in the barrel by holding the capsule over the open end 28 of the barrel and breaking the capsule shell thereby dropping the medication into the barrel. If the form of medication is not readily suspended in water, the syringe 20 crushes and/or grinds the medication as disclosed above.

It is understood that the above-described pill crushing method may be practiced without administering the dosage through the catheter into a tube. Alternatively, the suspension may be delivered to a tissue site, for example, or elsewhere as needed or desired.

It is further understood that the syringe 20 may be intended for single use application, made of plastic or other suitable disposable material, and disposed of after one usage to eliminate cross-contamination. Further, the syringe may comprise an electric pill crusher with removable plastic inserts or surfaces for the plunger, barrel, and/or catheter, the removable plastic inserts being replaceable for single use application. In this variation, the plunger can be electrically advanced and rotated to crush the pill, withdrawn to mix the suspension, and even advanced a second time to administer.

Figure 9:
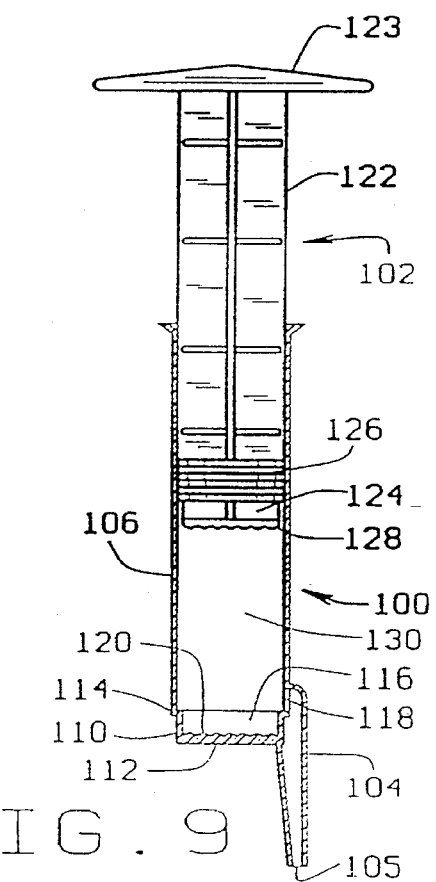
FIG. 9 is a cross-sectional view of the pill crushing syringe of the present invention illustrating the bi-level barrel, the bi-level plunger and the substantially straight side mounted catheter.

Building on the invention disclosed in the parent, the inventors have improved on their earlier pill crushing syringe by providing a syringe including a bi-level barrel 100, a mating bi-level plunger 102, and a substantially straight side mounted catheter 104 oriented substantially parallel to barrel 100 and having a tip end 105 (see FIG. 9) extending beyond closed end 112. The term "bi-level barrel" shall herein refer to a barrel having a first or standard interior diameter section 106, a reduced interior diameter section 110 having a closed end 112, a transition 114 between the first diameter section 106 and the reduced diameter section 110, and with a pocket 116 being thereby formed between the closed end 112 and the transition 114. In the preferred embodiment, an aperture 118 is formed through the first diameter section 106 and adjacent the transition 114, and the catheter 104 is connected around and extends from the aperture 118. Both sections 106 and 110 of the bi-level barrel 100 preferably have a cylindrical wall, and an abraded surface 120 is preferably located on the closed end 112.

The term "bi-level plunger" shall herein refer to a plunger having a first or standard exterior diameter section 122 with a handle 123, a reduced exterior diameter tip section 124 and a sealing gland 126 on the first diameter section 122 providing an air-tight relationship between the plunger 102 and the barrel 100. Although shown on plunger 102, the sealing gland 126 may instead be formed in barrel 100, or as part of both. In the preferred embodiment, the reduced diameter tip section 124 includes an abraded surface 128 positioned to engage the barrel abraded surface 120 as the plunger is advanced within the barrel. A cavity or space 130 is defined within the barrel 100 between the abraded surfaces 120 and 128, and the aperture 118 creates a fluid connection between the cavity 130 and the catheter 104.

The bi-level barrel 100 and the bi-level plunger 102 are adapted to allow the plunger tip section 124 to mate with and rotate within the barrel pocket 116 such that a pill may be crushed and/or ground between the abraded surfaces 120 and 128. In the preferred embodiment, the handle 123 is appropriately sized to allow a typical human hand to develop sufficient torque about the plunger axis to easily grind the pill between the abraded surfaces 120 and 128. The barrel and plunger may also include a threaded fitting (similar to the threaded fitting 47 shown in FIG. 2) to create a positive grinding action as the plunger is advanced by being rotated within the barrel.

In operation, the plunger 102 is removed from the barrel 100 to allow medication, preferably a pill (not shown), to be placed within the barrel, the plunger is advanced and rotated in the barrel lodging the pill between the abraded surfaces 120 and 128 and facilitating crushing and grinding of the pill into a powder. Holding the syringe substantially upright ensures that the powder (pill crushings) remains in the pocket 116 which is below the aperture 118 in this arrangement. This prevents the medication from escaping the barrel via the catheter 104 prior to aspiration. While the preferred embodiment includes the pocket 116 within bi-level barrel 100, it is understood that the pocket is not essential to maintaining high dosage integrity. In this embodiment, spacing the aperture 118 from the closed barrel end 112 prevents the pill crushings from escaping through the catheter 104 prior to aspiration. The sealing gland 126 allows a liquid to be drawn into the barrel 100 by withdrawing the plunger 102 from the barrel as the catheter tip 105 is submerged in a liquid. If desired, the syringe may be shaken to further mix the suspension. The barrel may then be flushed, and the suspension comprising the crushed pill and the liquid evacuated from the syringe by advancing the plunger into the barrel thereby forcing the suspension through the catheter.

Figure 10:
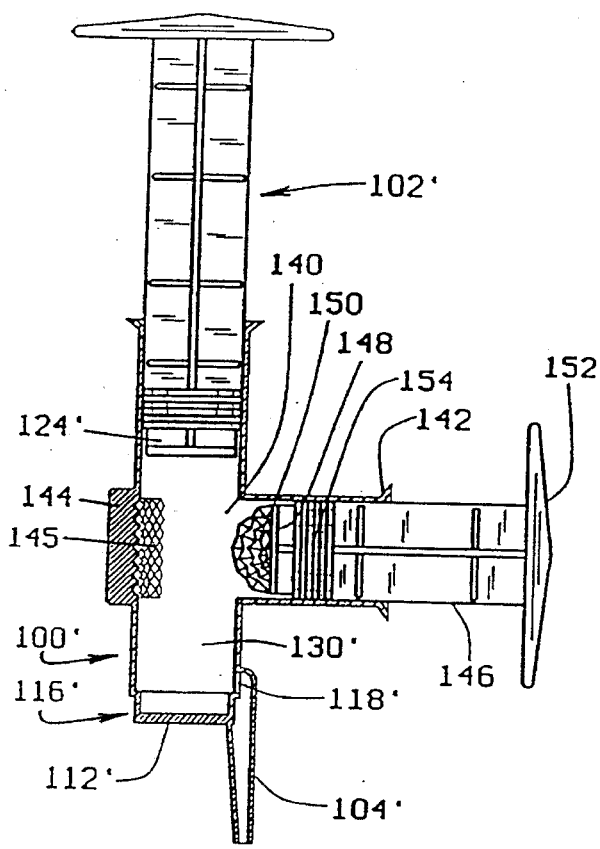
FIG. 10 is a cross-sectional view of an alternative embodiment of the invention illustrating the barrel having a side entry plunger.
Figure 12:
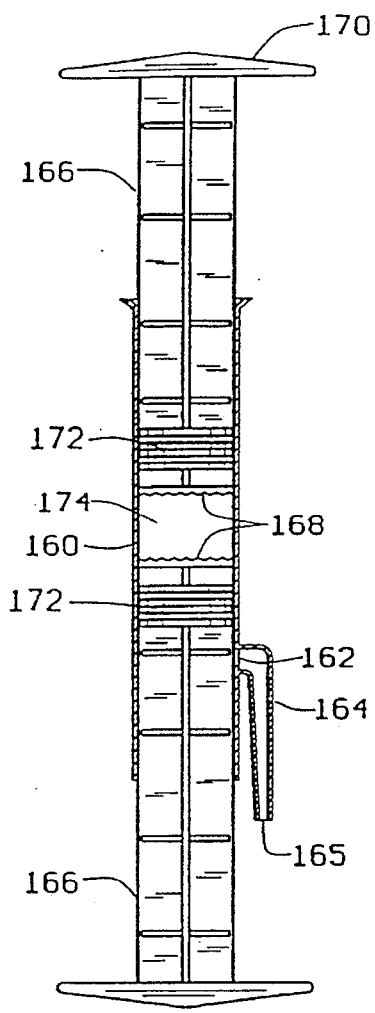
FIG. 12 is a cross-sectional view of another alternative embodiment of the invention illustrating a double barrel syringe.

An alternative embodiment of the present invention is illustrated in FIG. 10 and includes a bi-level barrel 100' having a closed end 112', a pocket 116' and an aperture 118' adjacent the pocket, a catheter 104' connected around and extending from the aperture 118', and a mating bi-level plunger 102'. A space or cavity 130' is defined within the barrel 100' between the plunger 102' and the closed end 112'. The bi-level barrel 100' further includes a side opening 140, a hollow side arm 142, and a reinforced barrel wall section 144 opposite the side opening 140. The reinforced barrel wall section 144 includes an interior abraded surface 145 which generally conforms to the shape of the barrel wall, allowing the plunger 102' to pass thereby. A side entry plunger 146 is movable within the side arm 142 and includes a tip end 148 having a convex abraded surface 150 thereon, a handle end 152, and may include a sealing gland 154. The abraded surface 145 is shaped and positioned to engage the convex side entry plunger abraded surface 150.

In operation, a pill is inserted into the barrel 100' by removing the plunger 102' or the side entry plunger 146. The plunger 102' is positioned to allow the side entry plunger 146 access to the cavity 130'. The syringe may then, if not already, be oriented horizontally. The pill is positioned between the side entry plunger 146 and the abraded surface 145, the side entry plunger 146 is advanced into the cavity 130' and may be rotated therein to thereby crush and/or grind the pill into a powder between the abraded surfaces 145 and 150. The side entry plunger 146 is then withdrawn from within the cavity 130' but is preferably not removed from the side arm 142. The syringe is then re-oriented substantially upright thereby causing the crushed pill ingredients to drop into the pocket 116'. The syringe may be lightly tapped to dislodge pill crushings remaining on the abraded surface 145. The bi-level plunger 102' is gently advanced completely into the barrel 100' to avoid blowing the pill crushings out through the catheter 104' and aspiration is performed substantially as explained above. Alternatively, the side entry plunger 146 may be used to aspirate the cavity 130'.

As illustrated in FIG. 10, the plunger 102' and barrel closed end 112' preferably do not have abraded surfaces in this embodiment. However, an abraded surface may be added to the plunger 102' and/or closed end 112' to assist in further crushing or grinding the pill ingredients deposited in the pocket 116' prior to aspiration. Also, these abraded surfaces can be used to crush a pill if desired. Threaded fittings may be included between the plunger 102' and the barrel 100' and/or the side entry plunger 146 and the side arm 142 to create a more positive grinding action as the plunger 102' or 146 is rotated. The threaded fittings in this embodiment are preferably similar to the threaded fitting 47 shown in FIG. 2.

Figure 11:
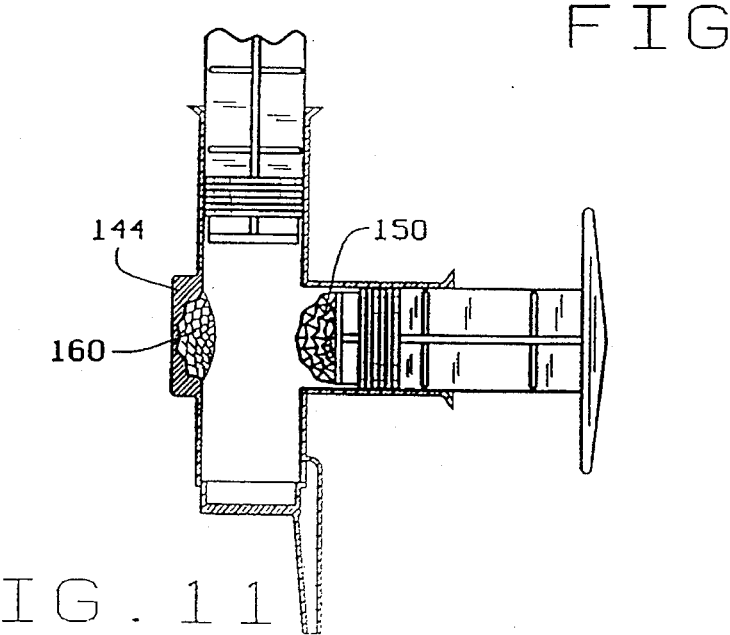
FIG. 11 is a cross-sectional view of a variation of the alternative embodiment shown in FIG. 10 illustrating a concave interior abraded surface opposite the side entry plunger.

A variation of this embodiment incorporates a concave interior abraded surface 160 (see FIG. 11). The concave abraded surface 160 is shaped, sized, and positioned to closely engage the convex side entry plunger abraded surface 150. This relationship assists in centering the pill between the abraded surfaces 150 and 160 and achieving a more thorough crushing of the pill.

Another alternative embodiment of the present invention is illustrated in FIG. 11. This embodiment provides a cylinder 160 having an aperture 162 through the cylinder wall and a catheter 164 connected around and extending from the aperture 162. The catheter 164 includes a tip end 165. Two plungers 166 having opposing abraded tip ends 168 are movable and rotatable within the cylinder 160. Each plunger 166 includes a handle 170 and a sealing gland 172. The sealing glands create a substantially air-tight relationship between the plungers 166 and the cylinder 160. A cavity or space 174 is defined within the cylinder 160 between the opposed abraded tip ends 168.

In operation, one of the plungers 166 is removed from the cylinder 160 and a pill is placed therein. The plunger is placed back into the cylinder and both plungers are preferably advanced toward one another within the cylinder such that the pill is positioned adjacent both abraded tip ends 168 while the space 174 is not aligned with the aperture 162. To facilitate plunger movement, aperture 162 may be kept in communication with space 174 until just before the pill is crushed. The plungers 166 are next rotated and pushed further together thereby crushing and grinding the pill into a powder. The plungers are simultaneously moved within the syringe until the space 174 is in fluid communication with the aperture 162. To minimize loss of pill crushings, space 174 may be oriented just out of communication with aperture 162 to thereby minimize the distance for travel by the two plungers in order to re-establish communication. At this point, the plungers are preferably as close together as possible. One or both of the plungers is then gently pulled away from the other while the catheter tip 165 is submerged in a liquid thereby drawing the liquid into the cylinder 160 and suspending the pill crushings in the liquid. The syringe is then positioned as desired for administering the pill and the suspension may then be flushed from the cylinder by advancing one or both of the plungers toward the other.

To further emphasize what is implicit in the parent hereto, as cross-referenced above, the term "pill" as used herein includes tablets, capsules, and other discrete units of medication, cooking herbs, spices, and similar solids. The pill may also include particles, powder, or liquid forms of medication, cooking herbs, spices, or similar substances. Moreover, while the preferred embodiment describes administering the suspension by forcing the suspension through the catheter and into a tube attached to a patient, it is understood that the invention may be practiced without administering the suspension through a tube. For instance, the suspension may be administered orally, rectally, delivered to a tissue site, or used in basting or other types of food preparation. Further, the invention is applicable to both human and veterinary applications (i.e. the suspension may be administered directly from the catheter into the mouth of an animal).

Although illustrated embodiments of the present invention are described herein with reference to the accompanying drawings, it is to be understood that the invention is not limited to those precise embodiments and that various other changes and modifications may be effected therein by one skilled in the art without departing from the scope or spirit of the invention. The scope of the invention is defined solely by the claims, and their equivalents.

What is claimed is:

1. A pill crushing syringe comprising a barrel having an aperture to facilitate drawing a liquid into the barrel and expelling the liquid therefrom, a plunger moveable within said barrel, at least one abraded surface within said syringe, and a threaded fitting between said barrel and said plunger, the threaded fitting advancing said plunger into said barrel as said plunger is rotated therein so that a pill placed within said syringe and adjacent said abraded surface is crushed as said plunger is rotated within the barrel.

2. The pill crushing syringe of claim 1 wherein the barrel includes at least one abraded surface and the plunger includes at least one abraded surface.

3. The pill crushing syringe of claim 2 wherein the two abraded surfaces are located in opposition to each other so that as said plunger is rotated, the abraded surfaces are advanced towards each other to crush said pill.

4. The pill crushing syringe of claim 3 wherein said barrel includes an open end and a closed end, the syringe further comprising a space between said plunger and said barrel closed end, an aperture through said barrel communicating with said space, a catheter in fluid communication with said aperture, and a sealing gland on either of said barrel or plunger so that a liquid may be drawn through said catheter and into said space by withdrawing said plunger from within said barrel as said catheter is submerged in said liquid.

5. A pill crushing syringe comprising a barrel having a side wall and a closed end, an aperture through said side wall and a catheter connected around and extending from said aperture, a plunger movable within said barrel, and at least one abraded surface within said syringe so that a pill placed within said syringe and adjacent said abraded surface is crushed as said plunger is moved within the barrel.

6. The pill crushing syringe of claim 5 further comprising a sealing gland on either of said barrel or said plunger wherein said aperture is positioned in spaced relation to said closed end so that as a pill is crushed its crushings may be accumulated adjacent said closed end and away from said aperture.

7. The pill crushing syringe of claim 6 wherein said at least one abraded surface is located on either of said barrel closed end or on a tip end of said plunger.

8. The pill crushing syringe of claim 7 further comprising a pair of opposing abraded surfaces located on said barrel closed end and said plunger tip end.

9. The pill crushing syringe of claim 8 wherein said catheter comprises a generally elongated tube extending substantially parallel to said barrel and extending beyond the barrel closed end.

10. The pill crushing syringe of claim 6 wherein said barrel further comprises a bi-level barrel and said plunger further comprises a bi-level plunger.

11. A pill crushing syringe comprising a bi-level barrel, a mating bi-level plunger movable within said barrel, and at least one abraded surface within said syringe so that a pill placed within said syringe and adjacent said abraded surface is crushed as said plunger is moved within the barrel.

12. The pill crushing syringe of claim 11 further comprising an aperture through said barrel, a catheter in fluid communication with said aperture, and a sealing gland on either of said barrel or plunger so that a liquid may be drawn through said catheter and into said barrel by withdrawing said plunger from within said barrel as said catheter is submerged in a liquid.

13. The pill crushing syringe of claim 12 wherein said barrel further includes a closed end, said barrel having a reduced diameter section nearest said closed end, said plunger having a reduced diameter section at a tip end for mating to said barrel reduced diameter section, and said aperture being located adjacent to but outside of said reduced diameter section.

14. The pill crushing syringe of claim 13 wherein said barrel includes at least one abraded surface and said plunger includes at least one abraded surface.

15. The pill crushing syringe of claim 14 wherein said plunger abraded surface is positioned to engage said barrel abraded surface as said plunger is advanced therein.

16. The pill crushing syringe of claim 15 wherein said barrel abraded surface is located on said closed end, and wherein said plunger abraded surface is located on said tip end.

17. The pill crushing syringe of claim 16 wherein said barrel permits the rotation of said plunger therein to thereby facilitate the grinding of a pill between the abraded surfaces.

18. A pill crushing syringe comprising a barrel having an open end, a closed end, and a side opening, a first plunger movable within said barrel through said open end, a side entry plunger movable within said barrel through said side opening, and at least one abraded surface within said syringe so that a pill placed within said syringe and adjacent said abraded surface may be crushed as at least one of said plungers is moved within the barrel.

19. The pill crushing syringe of claim 18 wherein at least one of said plungers includes said at least one abraded surface.

20. The pill crushing syringe of claim 19 wherein said barrel further includes at least one abraded surface positioned to engage the plunger abraded surface as said plunger abraded surface is advanced within said barrel.

21. The pill crushing syringe of claim 20 wherein said barrel permits the rotation of said plunger having said abraded surface to thereby facilitate the grinding of a pill between the abraded surfaces.

22. The pill crushing syringe of claim 21 wherein at least one of said open end or said side opening includes a threaded fitting, said threaded fitting advancing its associated plunger into the barrel as the plunger is rotated therein, thereby creating a positive grinding action between the abraded surfaces.

23. The pill crushing syringe of claim 22 further comprising a space between said closed end and said first plunger, a catheter, a fluid connection between said catheter and said space, and a sealing gland for sealing each of said plungers to said barrel so that a liquid may be drawn through the catheter and into said space by withdrawing either of said plungers from within said barrel as said catheter is submerged in the liquid.

24. A pill crushing syringe comprising a cylinder, two opposing plungers movable within said cylinder, and at least one abraded surface within said syringe so that a pill placed within said cylinder and adjacent said abraded surface is crushed as at least one of said plungers is moved within the cylinder.

25. The pill crushing syringe of claim 24 further comprising an aperture through said cylinder, a catheter in fluid communication with said aperture, and a sealing gland for sealing each of said plungers with said cylinder so that a liquid may be drawn through said catheter and into said cylinder by withdrawing at least one of said plungers from within said cylinder as said catheter is submerged in a liquid.

26. The pill crushing syringe of claim 25 wherein each of said plungers includes an abraded surface, said plungers being rotatable within said cylinder so that a pill placed within said cylinder and between said plungers is crushed as said plungers advance towards each other.

27. A method of creating a suspension of pill crushings in a syringe comprising the steps of:

placing a pill within a barrel of the syringe, advancing a plunger within the barrel to bring at least one abraded surface into contact with the pill to thereby crush the pill against the at least one abraded surface, and drawing liquid into the barrel by withdrawing the plunger, thereby mixing the liquid with the pill crushings to create the suspension.

28. The method of claim 27 further comprising the step of flushing the suspension out of the syringe by advancing the plunger within the barrel.

29. The method of claim 28 wherein the syringe includes a catheter in fluid communication with the barrel, the step of drawing liquid including the step of submerging a tip end of said catheter into a liquid, and the step of flushing the suspension including the step of flushing the suspension out of the barrel through the catheter.

30. The method of claim 29 wherein the step of advancing the plunger includes the step of rotating the plunger to better grind the pill into smaller pieces.

31. The method of claim 30 wherein the plunger and the barrel have mating abraded surfaces and wherein the step of rotating the plunger includes the step of exerting pressure against the plunger as it engages the pill to thereby grind the pill between the mating abraded surfaces.

32. A method of administering a pill dosage through a tube into a patient, the method including the steps of:

providing a pill crushing syringe including a barrel and a plunger, the syringe having at least one abraded surface;

placing the pill into the barrel;

crushing the pill into a powder by advancing the plunger into the barrel to thereby bring the abraded surface into contact with the pill;

drawing liquid into the barrel by withdrawing the plunger from within the barrel to thereby suspend said powder in said liquid; and flushing the suspension out of the barrel by advancing the plunger within the barrel.

33. The method of claim 32 wherein the barrel includes an aperture and a catheter connected around and extending from the aperture, and the step of drawing liquid into the barrel further includes the step of submerging the catheter into a liquid.

34. The method of claim 33 wherein the step of flushing the suspension further includes the step of flushing the suspension through the catheter.

35. The method of claim 34 wherein the pill comprises a capsule which houses medication within a shell, and the step of placing the pill into the barrel further includes the steps of positioning the capsule over the barrel and breaking the capsule shell thereby dropping the medication into the barrel, and the step of crushing the pill further includes the step of crushing the medication.

36. The method of claim 34 wherein the barrel further includes an open end and a closed end, an abraded surface being located on the closed end, and wherein the plunger further includes a tip end, the plunger abraded surface being located on a tip end such that the plunger abraded surface is positioned to engage the barrel abraded surface as the plunger is advanced in the barrel, the step of crushing the pill further including:

rotating the plunger within the barrel to thereby grind the pill between the abraded surfaces.

* * * * *